United States Patent [19]

Ikekawa et al.

[11] Patent Number: 5,200,536
[45] Date of Patent: Apr. 6, 1993

[54] FLUORINE-CONTAINING VITAMIN D3 ANALOGUES

[75] Inventors: Nobuo Ikekawa; Takeo Taguchi, both of Tokyo, Japan; Yoko Tanaka, Delmar, N.Y.; Yoshiro Kobayashi, Tokyo; Yutaka Ohira, Tsukuba, both of Japan

[73] Assignee: Daikin Industries Ltd., Osaka, Japan

[21] Appl. No.: 832,888

[22] Filed: Feb. 10, 1992

[51] Int. Cl.⁵ .............................................. C07J 172/00
[52] U.S. Cl. ................................................... 552/653
[58] Field of Search ......................................... 552/653

[56] References Cited

U.S. PATENT DOCUMENTS 4,804,502 2/1989 Baggiolini et al. ................... 514/167

Primary Examiner—Marianne M. Cintins
Assistant Examiner—Kimberly J. Kestler
Attorney, Agent, or Firm—Birch, Stewart, Kolasch & Birch

[57] ABSTRACT

Fluorine-containing vitamin D3 analogues of the formula:

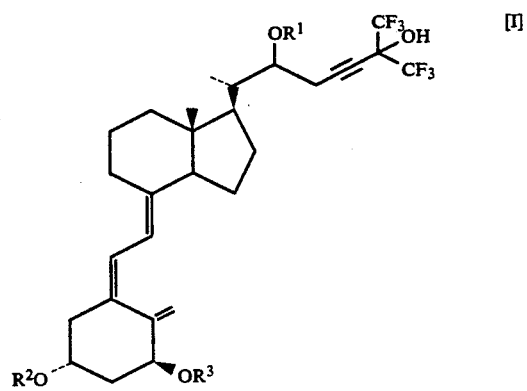

wherein $R^1$, $R^2$ and $R^3$ are independently hydrogen atom, a hydroxy-protecting group, having excellent pharmacological activities, such as tumor cell differentiation-inducing activity, which are useful as a medicament.

4 Claims, No Drawings

FLUORINE-CONTAINING VITAMIN D3 ANALOGUES

This invention relates to novel fluorine-containing vitamin D3 analogues which have excellent pharmacological activities, such as tumor cell differentiation-inducing activity and are expected to be used as a medicament.

PRIOR ART

It is known that a bio-metabolite of vitamin D3, 1α,25-dihydroxyvitamin D3 is called as "active-type vitamin D3" and has an activity of promoting absorption of calcium via intestinal tract and thereby is useful as a medicament for the treatment of bone diseases. Recently, it has been found that the active-type vitamin D and analogues thereof have a differentiation-inducing activity for recovering normal cells from cancerated cells (cf. Hirobumi Tanaka et al., "Seikagaku" (Biochemistry), Vol. 55, 1323, 1983) and further that some of these compounds have a remarked activity of inhibiting the progress of cancer (K. W. Colton et al., Lancet, Jan. 28, 188, 1989). It has, however, been known that these active-type vitamin D compounds have high antagonistic activity against calcium metabolism which induces hypercalcaemia and hence can not be used in a high dose. Accordingly, these compounds are not necessarily usable for the treatment of diseases which require continuous administration in a comparatively high dose, for example, for the treatment of leukemia.

SUMMARY DESCRIPTION OF THE INVENTION

The present inventors have intensively studied as to novel fluorine-containing vitamin D3 analogues which have excellent cell differentiation-inducing activity as well as high selectivity in calcium metabolism with less side effects, i.e. inhibition of hepercalcaemia.

An object of the invention is to provide novel fluorine-containing vitamin D3 analogues having pharmacological activities, especially anti-tumor activity owing to the cell differentiation-inducing activity. A further object of the invention is to provide a novel intermediate suitable for the preparation of the active fluorine-containing vitamin D3 analogues. These and other objects and advantages of the invention will be apparent to the skilled persons in this field from the following description.

DETAILED DESCRIPTION OF THE INVENTION

The fluorine-containing vitamin D3 analogues of this invention have the following formula [I]:

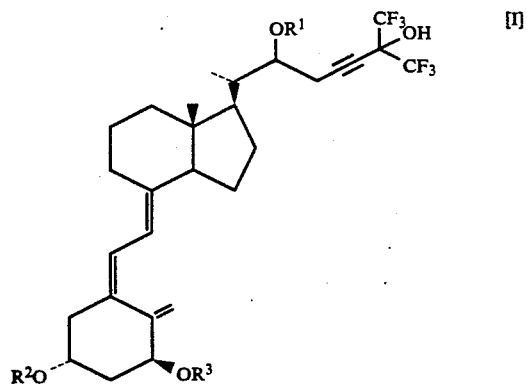

wherein $R^1$, $R^2$ and $R^3$ are independently hydrogen atom or a hydroxy-protecting group.

In the present specification and claims, the hydroxy-protecting group includes a group being capable of forming acetal type protecting group (e.g. methoxymethyl, ethoxyethyl, methoxyethoxymethyl, tetrahydropyranyl, etc.), a silyl ether type protecting group (e.g. trimethylsilyl, t-butyldimethylsilyl, t-butyldiphenylsilyl, etc.), an acyl group (e.g. acetyl), and the like.

Suitable examples of the compounds [I] are as follows.

1) Compound A: 26,26,26,27,27,27-Hexafluoro-24-homo-24-yne-1α,22S,25-trihydroxyvitamin D3

2) Compound B: 26,26,26,27,27,27-Hexafluoro-24-homo-24-yne-1α,22R,25-trihydroxyvitamin D3

3) 1α,3,22-Tris(t-butyldimethylsilyl) ether of Compound A
4) 1α,3,22-Tris(t-butyldimethylsilyl) ether of compound B The compounds [I] of this invention can be prepared by various processes. One of the best processes is illustrated below.

A [ring C,D] fragment of the formula [II]:

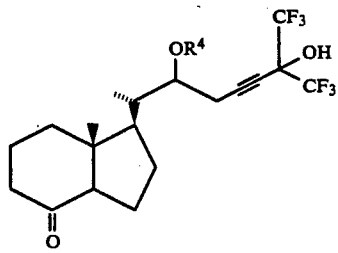
[II]

wherein $R^4$ is a hydroxy-protecting group, is subjected to coupling reaction with an anion derived from a protected [ring A] fragment of the formula [III]:

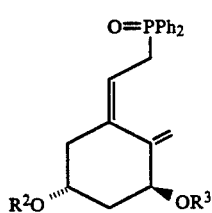
[III]

wherein $R^2$ and $R^3$ are each a hydroxy-protecting group, and Ph means phenyl, to give a condensed product of the formula of this invention.

The above coupling reaction of the compound [II] and the compound [III] is usually carried out at a low temperature, for example $-100°$ C. to $-50°$ C., preferably $-78°$ C. to $-20°$ C., in an ether solvent (e.g. diethyl ether, tetrahydrofuran (THF), etc.). The conversion if the [ring A] fragment into the corresponding carbanion is carried out by treating the fragment with an appropriate base such as an alkyl-lithium (e.g. n-butyllithium, etc). The reaction time is for 10 minutes to 24 hours, preferably for 30 minutes to 2 hours. The obtained product [I] can be purified by a conventional method, for example, by silica gel column chromatography. The removal of the hydroxy-protecting group from the compound [I] can optionally be carried out by a conventional method.

Starting compound [II] can be prepared by the process as illustrated by the following reaction scheme:

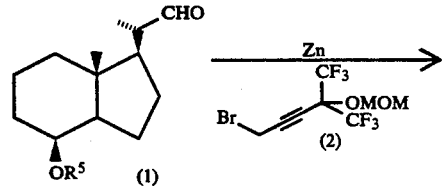

-continued

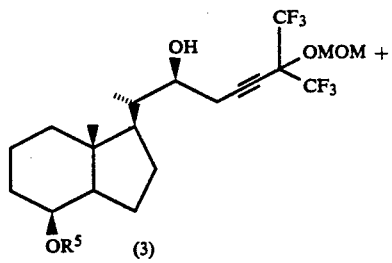
(3)

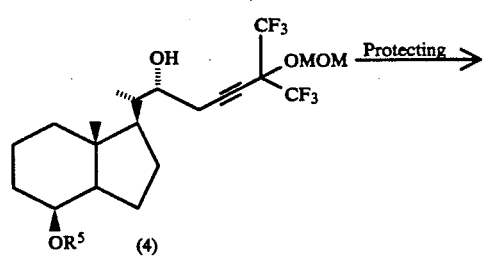
(4) Protecting →

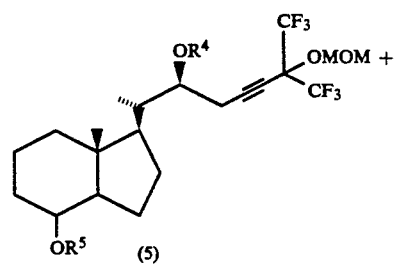
(5)

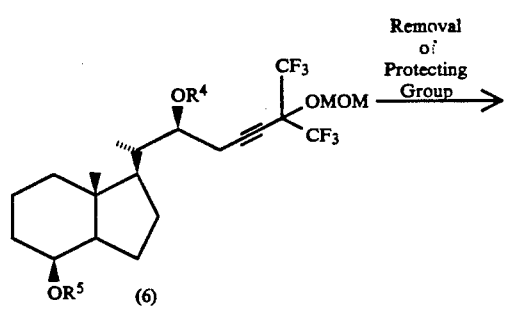
(6) Removal of Protecting Group →

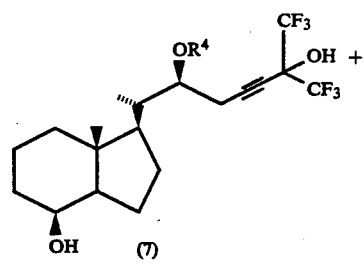
(7)

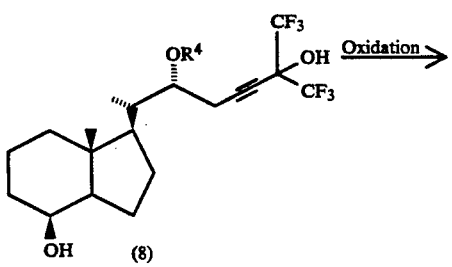
(8) Oxidation →

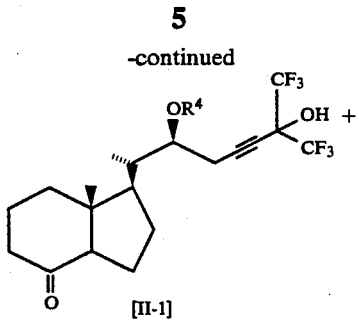

wherein R[4] and R[5] are each a hydroxy-protecting group, and MOM means methoxymethyl group.

According to the above process, the starting compound [II] ([II-1] and [II-2]) can be prepared by reacting the aldehyde compound (1) with the bromide compound (2) to give the compounds (3) and (4), protecting the hydroxy group of the resultant compounds (3) and (4) with a hydroxy-protecting group in a usual manner, removing the hydroxy-protecting group R[4] from the resultant compounds (5) and (6), and finally oxdizing the resultant compounds (7) and (8).

The compounds of this invention are illustrated by the following Examples and Reference Examples, but should not be constructed to be limited thereto.

EXAMPLE 1

1—1) Preparation of 1α,3-bis(t-butyldimethylsilyl) ether of compound (A) by Wittig reaction of compound [II-1] wherein R[4] is acetyl and compound [III] wherein R[2] and R[3] are t-butyldimethylsilyl:

To a solution of the compound [III] wherein R[2] and R[3] are t-butyldimethylsilyl (1.0 g) in anhydrous THF (10 ml) is added n-BuLi (2.5M, 0.68 ml) at −78° C., and the mixture is stirred for 5 minutes. To the solution is added a solution of the compound [II-1] wherein R[4] is acetyl (80 mg) in anhydrous THF (5 ml) is added and the mixture is stirred for 10 minutes after warming to room temperature. To the reaction mixture is poured a saturated ammonium chloride solution and the mixture is extracted with ethyl acetate. The ethyl acetate layer is washed with water and dried over anhydrous magnesium sulfate. After distilling off the solvent, the residue is purified by column chromatography to give the desired compound (106.9 mg, 78%) as a colorless solid.

$^1$H-NMR (CDCl$_3$) δ: 0.05 (s, 6 H), 0.06 (s, 6 H), 0.54 (s, 3 H), 0.866 (s, 9 H), 0.875 (s, 9 H), 0.94 (d, J=7.1 Hz, 3 H), 4.86 (d, J=2.8 Hz, 1 H), 5.18 (d, J=2.8 Hz, 1 H), 6.03 (d, J=12.2 Hz, 1 H), 6.24 (d, J=12.2 Hz, 1 H)

IR (KBr): 3431, 2954, 1221, 834 cm$^{-1}$ 1-2) Preparation of compound (A) by removal of the protecting silyl group:

The silyl compound obtained in Example 1—1 (99 mg) is added to a suspension of ion-exchange resin (50 W×4, 3 g) in methanol (30 ml) and stirred for 24 hours at room temperature. After filtrating the solution and distilling off the solvent, the residue is purified by column chromatography to give the desired compound (A) (66 mg).

$^1$H-NMR (CDCl$_3$) δ: 0.58 (s, 3 H), 0.91 (d, J=5.6 Hz, 3 H), 3.85–4.40 (m, 3 H), 4.91 (brs, 1 H), 5.29 (brs, 1 H), 6.11 (d, J=12 Hz, 1 H), 6.34 (d, J=12 Hz, 1 H)

IR (KBr): 3383, 2948, 1221, 858 cm$^{-1}$

EXAMPLE 2

Preparation of compound (B) from compound [II-2] wherein R[4] is acetyl:

Following the procedure of Example 1 except substituting compound [II-2] for compound [II-1], the desired compound (B) is obtained as a colorless solid.

$^1$H-NMR (CDCl$_3$) δ: 0.56 (s, 3 H), 0.95 (d, J=6 Hz, 3 H), 2.59 (dd, J=11 Hz, 3 Hz), 2.85 (dd, J=11 Hz, 3 Hz), 3.94 (m, 1 H), 4.23 (m, 1 H), 4.43 (m, 1 H), 5.00 (brs, 1 H), 5.33 (brs, 1 H), 6.02 (d, J=11 Hz, 1 H), 6.37 (d, J=11 Hz, 1 H)

REFERENCE EXAMPLE 1

Preparation of compound (3) and (4) wherein R[5] is t-butyldimethylsilyl by reacting compound (1) wherein R[5] is t-butyldimethylsilyl with compound (2):

To a solution of the aldehyde compound (1) wherein R[5] is t-butyldimethylsilyl group (1.14 g) and the bromide compound (2) (2.30 g) in DMF (8 ml) is added zinc powder (0.59 g) at 25° C. and the mixture is stirred for 30 minutes. After adding a saturated ammonium chloride solution, the mixture is extracted with ether. The ether layer is washed with water and dried over anhydrous magnesium sulfate. After distilling off the solvent, the residue is purified by column chromatography to give the desired compound (3) (1.36 g) and the compound (4) wherein R[5] is t-butyldimethylsilyl (0.54 g).

As to compound (3): $^1$H-NMR (CDCl$_3$) δ0.00 (s, 3 H), 0.01 (s, 3 H), 0.01 (s, 3 H), 0.90 (s, 9 H), 0.91 (d, J=5 Hz, 3 H), 0.91 (s, 3 H), 2.32 (dd, J=17 Hz, 5 Hz, 1 H), 2.60 (dd, J=17 Hz, 9 Hz, 1 H), 3.47 (s, 3 H), 3.95 (m, 1 H), 4.00 (brs, 1 H), 5.07 (d, J=25 Hz, 1 H), 5.09 (d, 25 Hz, 1 H)

IR (KBr): 3470, 2250, 1230 cm$^{-1}$

As to compound (4): $^1$H-NMR (CDCl$_3$) δ: 0.00 (s, 3 H), 0.01 (s, 3 H), 0.89 (s, 9 H), 0.93 (d, J=5 Hz, 3 H), 0.95 (s, 3 H), 3.48 (s, 3 H), 3.89 (m, 1 H), 4.00 (brs, 1 H), 5.08 (d, J=25 Hz, 1 H), 5.10 (d, J=25 Hz, 1 H)

IR (CHCl$_3$) 3520, 2260, 1230 cm$^{-1}$

REFERENCE EXAMPLE 2

Preparation of compound (5) wherein R[4] is acetyl and R[5] is t-butyldimethylsilyl by protecting compound (3) obtained in Reference Example 1:

A solution of the alcohol compound (3) obtained in Reference Example 1 (149 mg), acetic anhydride (0.7 ml), pyridine (1.2 ml) and 4-dimethylaminopyridine (35 mg) in dichloromethane (2.5 ml) is stirred for 18 hours at room temperature. After completing the reaction, the mixture is extracted with ether, the ether extract is washed with 2% HCl, 5% sodium bicarbonate solution and brine. After distilling off the solvent, the residue is purified by column chromatography to give the desired compound (5) wherein R[4] is acetyl and R[5] is t-butyldimethylsilyl (140 mg).

$^1$H-NMR (CDCl$_3$) δ: 0.00 (s, 6 H), 0.88 (s, 9 H), 0.90 (s, 3 H), 0.96 (d, J=6.8 Hz, 3 H), 2.05 (s, 3 H), 3.43 (s, 3 H), 3.98 (brs, 1 H), 5.03 (s, 2 H), 5.08 (m, 1 H)

IR (neat): 2956, 2256, 1747, 1472, 1376 cm$^{-1}$

REFERENCE EXAMPLE 3

Preparation of compound (6) wherein $R^4$ is acetyl and $R^5$ is t-butyldimethylsilyl by protecting compound (4) obtained in Reference Example 1:

Following the procedure of Reference Example 2 except substituting the compound (4) obtained in Reference Example 1 for the compound (3), the desired compound (6) wherein $R^4$ is acetyl and $R^5$ is t-butyldimethylsilyl is obtained.

$^1$H-NMR (CDCl$_3$) δ: 0.00 (s, 3 H), 0.01 (s, 3 H), 0.88 (s, 9 H), 0.92 (s, 3 H), 0.93 (d, J=7 Hz, 3 H), 2.03 (s, 3 H), 2.53 (m, 2 H), 3.43 (s, 3 H), 4.01 (brs, 1 H), 5.02 (d, J=25 Hz, 1 H), 5.04 (d, J=25 Hz, 1 H), 5.11 (m, 1 H)

Melting Point: 74.3° C. to 75.5° C. (ethanol)

REFERENCE EXAMPLE 4

Preparation of compound (7) wherein $R^4$ is acetyl by removal of the protecting group of compound (5) obtained in Reference Example 2:

A mixture of the acetate compound (5) obtained in reference Example 2 (200 mg), dichloromethane (2.4 ml), acetic acid (2.4 ml) and 5% HCl (0.4 ml) is refluxed for 5 hours. After completing the reaction, the mixture is extracted with ethyl acetate, and the extract is washed with 5% sodium bicarbonate solution and dried over magnesium sulfate. After distilling off the solvent, the residue is purified by column chromatography to give the desired compound (7) wherein $R^4$ is acetyl (65 mg, 44%).

$^1$H-NMR (CDCl$_3$) δ: 0.94 (s, 3 H), 0.98 (d, J=6.8 Hz, 3 H), 2.09 (s, 3 H), 4.09 (brs, 1 H), 4.77 (s, 1 H), 5.23 (m, 1 H)

IR (KBr): 3545, 3219, 2937, 1719, 1250, 1200, 958 cm$^{-1}$

REFERENCE EXAMPLE 5

Preparation of compound (8) wherein $R^4$ is acetyl by removal of the protecting group of compound (6) obtained in Reference Example 3:

Following the procedure of Reference Example 4 except substituting the compound (6) obtained in Reference Example 3 for the compound (5), the desired compound (8) wherein $R^4$ is acetyl is obtained.

$^1$H-NMR (CDCl$_3$) δ: 0.96 (s, 3 H), 0.97 (d, J=7 Hz, 3 H), 2.07 (s, 3 H), 2.46 (m, 2 H), 4.09 (brs, 1 H), 5.20 (m, 1 H)

Melting point: 156° C. to 157.5° C. (ether/hexane)

REFERENCE EXAMPLE 6

Preparation of compound [II-1] wherein $R^4$ is acetyl by oxidation of compound (7) obtained in Reference Example 4:

To a solution of pyridinium chlorochromate (PCC, 50 mg) in dichloromethane (2 ml) is added a solution of alcohol compound (7) obtained in Reference Example 4 (21 mg) in dichloromethane (2 ml), and the mixture is stirred for 4 hours at room temperature. After adding ether, the mixture is filtered. After distilling off the solvent of the filtrate, the residue is purified by column chromatography to give the desired compound [II-1] wherein $R^4$ is acetyl (18.9 mg, 91%).

$^1$H-NMR (CDCl$_3$) δ: 0.64 (s, 3 H), 1.04 (d, J=6.6 Hz, 3 H), 2.10 (s, 3 H), 4.53 (brs, 1 H), 5.22 (m, 1 H)

IR (neat): 3262, 2964, 2252, 1738, 1713, 1698, 1240, 957 cm$^{-1}$

REFERENCE EXAMPLE 7

Preparation of compound [II-2] wherein $R^4$ is acetyl by oxidation of compound (8) obtained in Reference Example 5:

Following the procedure of Reference Example 6 except substituting the compound (8) obtained in Reference Example 5 for the compound (7), the desired compound [II-2] is obtained.

$^1$H-NMR (CDCl$_3$) δ: 0.65 (s, 3 H), 1.05 (d, J=7 Hz, 3 H), 3.26 (brs, 1 H), 5.35 (dt, J=15 Hz, 1 H), 5.45 (dd, J=15 Hz, 5 Hz, 1 H)

EXPERIMENT

Test method:

Subculture cells (HT-29) derived from human colonic cancer were inoculated onto a 24-well plate for tissue culture and was cultured in RPMI-1640 medium (added with 10% fetal calf serum). After culturing for about 24 hours, the supernatant was removed. To the residue was added a medium containing $2 \times 10^{-3}$M sodium butyrate and 1α,25-dihydroxyvitamin D$_3$ or a vitamin D$_3$ analogue of this invention (exchange of the medium), and the mixture was subjected to station culture in a culture vessel containing carbon dioxide (5% CO$_2$-95% air) at 37° C. On every other day, the culture medium was exchanged with the same medium as mentioned above, and on 7th day, the number of the myxopoietic cells and shape of the cells were observed by the method of Augeron et al. [cf. *Cancer Res*, Vol. 44, 3961, 1984].

It is known that the myxopoiesis is observed in normal cells of large intestine (the colon) but not in cancerated HT-29 cells. Accordingly, as a marker for measuring the fact that the cancer cells HT-29 was differentiated and could express characteristic of normal cells, the number of mycopoietic cells was measured.

Results:

The data obtained above were shown in percentage based on whole cells (200 cells) measured. The results are shown in the following Table 1.

TABLE 1

| Test compound | Concentration (M) | Number of myxopoietic cells (%) |
| --- | --- | --- |
| Non | 0 | 3 ± 3 |
| 1,25-dihydroxy-vitamin D$_3$ | $10^{-7}$ | 100 |
| 1,25-dihydroxy-vitamin D$_3$ | $10^{-8}$ | 39 |
| Compound B | $10^{-7}$ | 90 ± 10 |
| Compound B | $10^{-8}$ | 91 ± 9 |
| Compound B | $10^{-9}$ | 49 ± 8 |

As is clear from the above results, when the HT-29 cells were treated by $2 \times 10^{-3}$M sodium butyrate and the compounds of this invention, the cells were differentiated into myxopoietic cells.

What is claimed is:

1. A fluorine-containing vitamin D$_3$ analogue of the formula [I]:

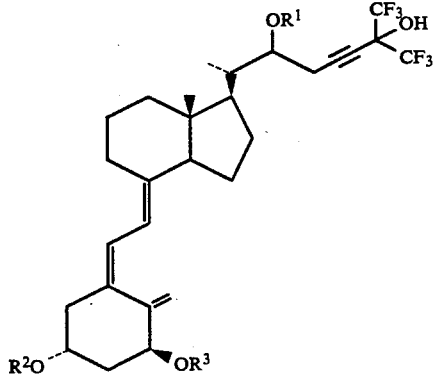

wherein R¹, R² and R³ are independently a hydrogen atom or a hydroxy-protecting group.

2. The compound according to claim 1, wherein the hydroxy-protecting group is selected from the group consisting of methoxymethyl, ethoxyethyl, methoxyethoxymethyl, tetrahydropyranyl, trimethylsilyl, t-butyldimethylsilyl, t-butyldiphenylsilyl, and acetyl.

3. The compound of claim 1 which has the formula:

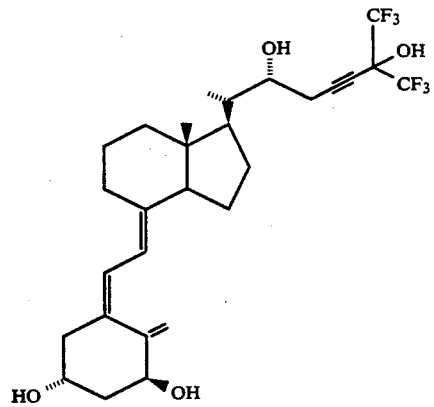

and 1α,3,22-tris(t-butyldimethylsilyl) ether thereof.

4. The compound of claim 1 which has the formula:

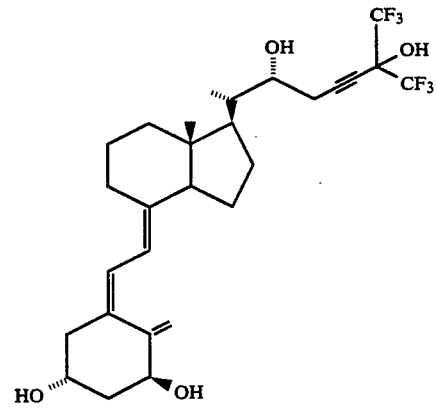

and 1α,3,22-tris(t-butyldimethylsilyl) ether thereof.

* * * * *